(12) United States Patent
Liphardt et al.

(10) Patent No.: US 8,339,603 B1
(45) Date of Patent: Dec. 25, 2012

(54) MAPPING ELLIPSOMETERS AND POLARIMETERS COMPRISING POLARIZATION STATE COMPENSATING BEAM DIRECTING MEANS, AND METHOD OF USE

(75) Inventors: Martin M. Liphardt, Lincoln, NE (US); Blaine D. Johs, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 495 days.

(21) Appl. No.: 12/587,190

(22) Filed: Oct. 2, 2009

Related U.S. Application Data

(60) Provisional application No. 61/195,068, filed on Oct. 3, 2008.

(51) Int. Cl.
*G01J 4/00* (2006.01)

(52) U.S. Cl. .................................................. 356/369
(58) Field of Classification Search .................. None
See application file for complete search history.

(56) References Cited

U.S. PATENT DOCUMENTS

| | | | |
|---|---|---|---|
| 5,517,312 A | 5/1996 | Finarov | 356/630 |
| 5,963,327 A | 10/1999 | He et al. | 356/369 |
| 5,969,818 A | 10/1999 | Johs et al. | 356/369 |
| 6,034,777 A | 3/2000 | Johs et al. | 356/369 |
| 6,549,282 B1 | 4/2003 | Johs et al. | 356/369 |
| RE38,153 E | 6/2003 | Finarov | 356/630 |
| 6,804,004 B1 | 10/2004 | Johs et al. | 356/369 |
| 7,277,171 B1 | 10/2007 | Johs et al. | 356/369 |
| 2004/0070760 A1 | 4/2004 | Stehle et al. | |

*Primary Examiner* — Gordon Stock, Jr.
(74) *Attorney, Agent, or Firm* — James D. Welch

(57) ABSTRACT

Mapping ellipsometer and polarimeter systems which comprise polarization state change compensating beam directing means.

17 Claims, 8 Drawing Sheets

US 8,339,603 B1

MAPPING ELLIPSOMETERS AND POLARIMETERS COMPRISING POLARIZATION STATE COMPENSATING BEAM DIRECTING MEANS, AND METHOD OF USE

This Application Claims Benefit of Provisional Application No. 61/195,068 Filed Oct. 3, 2008.

TECHNICAL FIELD

The present invention relates to mapping ellipsometer and polarimeter systems, and more particularly to mapping ellipsometer and polarimeter systems which comprise ellipsometric PSI and DELTA correcting beam directing means.

BACKGROUND

It is known to investigate samples at a multiplicity of locations thereon with electromagnetic beams, by applying ellipsometer and polarimeter systems. One approach is disclosed in a Patent to Johs et al., U.S. Pat. No. 7,277,171, which describes mounting an ellipsometer, polarimeter, reflectometer and the like on a means for enabling its motion in "X", "Y" and "Z" directions. Another approach is described in Patents to Finarov, (eg. U.S. Pat. No. 5,517,312, RE38,153) which describes providing a stationary ellipsometer and applying movable beam directing means to direct an electromagnetic beam to a multiplicity of locations on a sample, but the Finarov Patents are silent as to correcting effects of said beam direction on polarization state.

Before preceding, for general insight it is also noted that ellipsometer and polarimeter systems generally comprise Polarization State Generation (PSG) and Polarization State Detection (PSD) systems configured such that the (PSG) directs a polarized beam of electromagnetic radiation toward a sample, and the (PSD) detects a beam which emerges from said sample after interaction therewith. It is noted that the present invention provides utility in that the (PSG) and (PSD) can be oriented closely next to one another because of the operation of first and second dual reflection surface means, (eg. prisms). This enables convenient application to environmental chambers in which, for instance, deposition onto or etching from a sample is practiced. It is often difficult to provide a retrofit ellipsometer system to such chambers, and it all can be, for instance, through a single window, that can greatly simplify the task of performing, for instance, sample mapping.

Continuing, it is also mentioned that ellipsometric PSI and DELTA refer to well known changes in a ratio of polarized beam orthogonal components and phase angle therebetween, respectively, induced by interaction of the polarized electromagnetic beam with the sample.

Because the present invention can be practiced with beam directing means that operate based on Total Internal Reflection, or on Specular reflection, it is also disclosed that U.S. Pat. Nos. 6,034,777, 6,549,282 and 6,804,004 describe methodology for correcting polarizations state effects introduced by beam directing means that rely on specular reflection so that uncorrelated PSI and DELTA of a Sample being investigated can be achieved. Also, U.S. Pat. No. 5,969,818 and describes a four bounce mirror system which performs orthogonal component compensation, and U.S. Pat. No. 5,963,327 to He et al. and Published Application US 2004/0070760 by Stehle ey al. describe an ellipsometer or the like in which beam directing means allow a source and detector to be positioned side by side rather than distally from one another along the locus of a sample investigating beam. However, no known reference discloses a dual prism means configured to provide a polarized output beam in a "X"-"Z" plane, by re-directing an input beam which enters thereinto along a "Y" axis, in an "X"-"Y"-"Z" coordinate system which substantially compensates any effects on a Polarization State of a polarized beam of electromagnetic radiation entered thereinto.

The references identified above are all incorporated by reference into this Disclosure.

DISCLOSURE OF THE INVENTION

In the following, orthogonal "X"-"Y"-"Z" coordinates will be utilized to aid with description of a present invention system, however, it is to be appreciated that a so described present invention system can be translated and rotated about any of said demonstrative coordinates without altering its operation. Therefore, the present invention is not to be considered limited by the use of demonstrative "X"-"Y"-"Z" coordinates in the description thereof, to any specific laboratory coordinate system.

Continuing, the present invention is an ellipsometer, polarimeter or the like system which comprises a dual prism means configured to provide a polarized output beam in a "X"-"Z" plane, by re-directing an input beam which enters thereinto along a "Y" axis in an orthogonal "X"-"Y"-"Z" coordinate system. Said dual prism means further provides benefit in that it substantially compensates any effects on polarization state of a polarized beam of electromagnetic radiation entered by a interaction with a first beam directing reflection therewithin, by the effects of interaction with a second beam directing reflection therewithin. (Note Polarization State basically refers to a relationship between orthogonal p and s components in a polarized beam of electromagnetic radiation). This results because the effect of a first reflection on an orthogonal, (eg. p or s component), of a polarized beam in the dual prism means configuration, is canceled by a similar effect in the second reflection on the other, (eg. s or p component), respectively. For example, if the first reflection has an effect on the p component, the second reflection has a compensating effect on the component and vice-versa. It is noted that the just described compensation occurs as the planes of the reflective surfaces of the dual prism are perpendicular to one another.

It is also disclosed that the reflective surfaces of the dual prism can be coated with a material, (such as aluminum, but not limited to such), and the present invention will still function, but with different physics. Without the coating on the reflective surfaces the reflections are based on total internal reflection. With a coating present the reflective surfaces the reflections are based on specular reflection. In fact, it is to be understood that a system of two specularly reflecting means can replace the dual prisms, if the planes of incidence that a beam makes with respect to said two surfaces are perpendicular to one another, as are the reflective surfaces of the two prisms. When the reflections are specular, polarization state corrections of the effects thereof is described in U.S. Pat. Nos. 6,034,777, 6,549,282 and 6,804,004. These Patents describe methodology for correcting polarizations state effects introduced by beam directing means that rely on specular reflection, so that uncorrelated PSI and DELTA of a Sample being investigated can be achieved.

It is also to be appreciated that the dual prism means can be rotated about an axis parallel to the "Y" axis of the "X"-"Y"-"Z" coordinate system to alter the angle at which the output beam exits therefrom in the "X"-"Z" plane. Typically said rotation will be along the input beam locus which, as mentioned above, can be taken to approach along a "Y" axis. This enables adjusting the angle-of-incidence (AOI) of the exiting beam with respect to a sample positioned so that said output beam impinges thereonto.

Further, in addition to the first dual prism means described above, the present invention can involve a second dual prism means configured to receive a beam which reflects from a sample in a an "X"-"Z" plane, and re-direct it along a parallel to the "Y" axis into a detector. This enables providing an ellipsometer or polarimeter with polarization state generation and polarization state detection systems located adjacently, side by side, rather than distally positioned from one another.

The present invention is also an ellipsometer, polarimeter or the like system which comprises a first reflection means comprising two beam directing reflection surfaces oriented in orthogonally related planes with respect to one another. In use a polarized input beam entered thereto along a locus in a first beam plane reflects from both said reflective surfaces and exits from said first reflection means along a locus parallel to a plane which results from rotating said first beam plane about the locus of said polarized input beam. Reflection from the second beam directing reflection surface serves to substantially compensate any effects on beam polarization state entered by reflection from the first beam directing reflection surface, the mechanism thereof being that the effect of a first reflection on a p or s component of a polarized beam is canceled by a similar effect in the second reflection on an s or p component, respectively. Said first reflection means can be selected from the group consisting of:
- a first dual prism means configured to provide a polarized output beam along a locus parallel to a plane resulting from rotating said first beam plane about the locus of said input beam, said reflections being based on total internal reflection;
- a first dual prism means configured to provide a polarized output beam along a locus in a plane parallel to a plane resulting from rotating said said first beam plane about the locus of said input beam, said reflections being based on specular reflection.
- a first dual reflecting means comprising two beam directing reflective surfaces, other than in the context of a prisms, which are specularly reflecting and are configured to provide a polarized output beam along a locus parallel to a plane resulting from rotating said first beam plane about the locus of said input beam.

In any of said selections it is noted that the two beam directing reflective surfaces are oriented in planes which are perpendicular to one another.

Continuing, as an additional aspect, it is possible to position a plurality of first and second dual prism means adjacent to a sample, and move an ellipsometer or polarimeter polarization state generation and polarization state detection systems located adjacently, side by side, to sequentially provide and receive, respectively, input and output electromagnetic beams sequentially therefrom.

A present invention ellipsometer, polarimeter or the like system can also comprise polarization state generation and polarization state detection systems located adjacently, side by side, said ellipsometer, polarimeter or the like system further comprising a plurality of combinations of first and second dual prism means, each thereof being constructed as a selection from the group consisting of:
- each consists of two separate prisms; and
- each consists of a single element.

The first dual prism in each of the plurality thereof is associated with the polarization state generator such that a beam received thereby from the polarization state generator is directed to impinge on said sample. The second dual prism means in each of the plurality thereof being associated with the polarization state detector such that a beam reflecting from said sample is directed thereby to the polarization state detector. Said first and second dual prisms in each combination thereof are aligned with one another adjacent to said sample such that, in use, the first combination of first and second dual prism means is positioned to intercept an input beam such that a first location on the sample is investigated, and thereafter, the first combination of said first and second dual prism means can be moved to a position which allows the input beam to be intercepted by the second combination of first and second dual prism means so that a second location on the sample is investigated. Further, said second combination of first and second dual prism means can be also be moved out of the path of the input beam thereby allowing a third of combination of first and second dual prism means to intercept the input beam so that a third location on the sample can be investigated, and so on.

Additionally, a stationary ellipsometer or polarimeter polarization state generation and polarization state detection systems located adjacently, side by side, can have a single first and second dual prism means mounted with respect thereto to allow its motion in a direction parallel to the input beam locus so that a sequence of points along a line on a sample can be sequentially investigated. In this embodiment said single first and second dual prism means can be mounted to allow rotation along an axis parallel to the input beam locus, so that a sample comprising the inside of a pipe, or perhaps two samples oriented parallel to one another can be investigated.

Another embodiment provides that a single dual prism means be applied to direct both input and output beams. In this approach input and output beams are directed along a "Y" axis and the sample investigating beam approaches a sample along an angle of incidence in an "X"-"Z" plane. Between the single dual prism means and said sample is located a focusing means, the optical axis of which is off-set from a location which would direct the input beam along said focusing means optical axis. Further, a reflecting means is positioned to direct the input beam, after it reflects from the sample, back toward the sample so that it reflects from a different position thereon, then passes back through said focusing means, and back through the single dual prism means, (which can below separate prisms or a composite thereof). The effect of doing this is to cause the output beam to exit the single dual prism means offset from the input beam, so it can enter a detector which is offset from the source of the input beam.

It is noted that another embodiment of the present invention can apply a system comprising a stationary ellipsometer or polarimeter polarization state generation and polarization state detection systems located adjacently, side by side. Also present is a combination of at least one dual prism means and a reflection means mounted to allow both to be moved together in an "X" direction parallel to an input beam locus, but such that the at least one dual prism means can be moved in a "Z" direction perpendicular to said input beam locus. In use the combination of the at least one dual prism means and a reflection means mounted can be moved together in an "X" direction parallel to an input beam locus, and the at least one dual prism means can be moved in a "Z" direction perpendicular to said input beam locus to allow many points on an adjacent sample to be investigated.

A present invention method comprises the steps of:
a) providing an ellipsometer, polarimeter or the like system which comprises a first dual reflection surface means selected from the group consisting of:
   two separate reflection surfaces; and a single element having two reflection surfaces.

Said first dual reflection surface means is selected from the group consisting of:
   a first dual prism means configured to provide a polarized output beam along a locus parallel to a plane resulting from rotating said first beam plane about the locus of said input beam, said reflections being based on total internal reflection;
   a first dual prism means configured to provide a polarized output beam along a locus in a plane parallel to a plane resulting from rotating said said first beam plane about the locus of said input beam, said reflections being based on specular reflection.
   a first dual reflecting means comprising two beam directing reflection surfaces, which reflection surfaces are specularly reflecting and are configured to provide a polarized output beam along a locus parallel to a plane resulting from rotating said first beam plane about the locus of said input beam.

Said two beam directing reflection surfaces are oriented in planes which are perpendicular to one another and being configured to provide a polarized output beam in a "X"-"Z" plane, by re-directing an input beam which enters thereinto along a "Y" axis, in an "X"-"Y"-"Z" coordinate system. Said first dual reflection surface means further serves to substantially compensate any effects on beam polarization state entered by a first beam directing reflection therewithin, by the effects of a second beam directing reflection therewithin. The mechanism thereof is that the effect of a first reflection on a p or s component of a polarized beam in the dual reflection surface means configuration, is canceled by a similar effect in the second reflection on an s or p component, respectively.

Said first dual reflection surface means is mounted to allow rotation about an axis parallel to the "Y" axis of the "X"-"Y"-"Z" coordinate system to alter the angle at which the output beam exits therefrom, said rotation being along the input beam locus, which enables adjusting the angle-of-incidence (AOI) of the exiting beam with respect to a sample positioned so that said output beam impinges thereonto.

The method continues with:
b) causing a beam polarized beam to enter said first dual reflection surface means along a locus parallel to a "Y" axis, such that said beam reflects from twice therewithin and exits in an "X"-"Z" plane.

Said method can also provide that the step of providing an ellipsometer, polarimeter or the like system, further comprises, in addition to the first dual reflection surface means, a second dual reflection means positioned to receive a beam which reflects from a sample in an "X"-"Z" plane, and re-direct it parallel to said input beam "Y" axis into a detector, thereby enabling an ellipsometer or polarimeter with a polarization state generation and a polarization state detection system located adjacently, side by side.

Another present invention method comprises the steps of:
a) providing a system comprising:
   a1) a movable ellipsometer, polarimeter or the like system comprising:
      a polarization state generator; and
      a polarization state detector;
   oriented adjacently side by side and separated by a fixed predetermined distance therebetween, such that in use the position of said movable ellipsometer, polarimeter or the like system polarization state generator and polarization state detector can be moved as a unit;
   a2) a sample;
   a3) at least two beam directing means, each comprising first and second dual reflection surface means, selected from the group consisting of:
      two separate reflection surfaces; and
      a single element having two reflection surfaces.

Each of said first and second dual reflection surface means are configured to provide a polarized output beam in a "X"-"Z" plane, by re-directing an input beam which enters thereinto along a "Y" axis, in an "X"-"Y"-"Z" coordinate system. Said first dual reflection surface means further serves to substantially compensate any effects on beam polarization state entered by a first beam directing reflection therewithin, by the effects of a second beam directing reflection therewithin, the mechanism thereof being that the effect of a first reflection on a p or s component of a polarized beam in the dual reflection surface means configuration, is canceled by a similar effect in the second reflection on an s or p component, respectively.

The first and second dual reflection surface means in each beam directing are further oriented adjacently side by side and separated by a fixed predetermined distance therebetween which is appropriate to allow a beam of electromagnetic radiation from said polarization state generator to enter one thereof, be directed thereby to reflect from said sample, enter the second thereof, and be directed thereby into the polarization state detector.

The method continues with:
b) positioning said at least two beam directing means at locations offset from one another;
c) moving said movable ellipsometer, polarimeter or the like system into a position such that a beam of electromagnetic radiation from said polarization state generator enters one of said first and second dual reflection surface means of one of said beam directing means, is directed thereby to reflect from said sample, enter the other of said first and second dual reflection surface means thereof and be directed thereby into the polarization state detector;
d) moving said movable ellipsometer, polarimeter or the like system into a position such that a beam of electromagnetic radiation from said polarization state generator enters one of said first and second dual reflection surface means of the other of said beam directing means, is directed thereby to reflect from said sample, enter the other of said first and second dual reflection surface means thereof and be directed thereby into the polarization state detector;
to the end that said polarization state detector produces an output signal.

Said method can further involve the step of providing a system further involves providing at least a third beam directing means, which is functionally similar to the first and second beam directing means;
and wherein said method further comprises:
e) moving said movable ellipsometer, polarimeter or the like system into a position such that a beam of electromagnetic radiation from said polarization state generator enters one of said first and second dual reflection surface means of the third of said beam directing means, is directed thereby to reflect from said sample, enter the other of said first and second dual reflection surface means thereof and be directed thereby into the polarization state detector;
to the end that said polarization state detector produces an output signal.

Further, methodology of practicing the present invention involves causing a beam to enter said first dual reflection surface means along a locus parallel to a "Y" axis, such that said beam reflects from twice therewithin and exits in an "X"-"Z" plane, and can further include at least one selection from the group consisting of:

- storing at least some data provided by said data detector in machine readable media;
- analyzing at least some of the data provided by said data detector and storing at least some of the results of said analysis in machine readable media;
- displaying at least some data provided by said data detector by electronic and/or non-electronic means;
- analyzing at least some of the data provided by said data detector and displaying at least some of the results of said analysis by electronic and/or non-electronic means;
- causing at least some data provided by said data detector to produce a signal which is applied to provide a concrete and tangible result; and
- analyzing at least some of the data provided by said data detector and causing at least some thereof to produce a signal which is applied to provide a concrete and tangible result.

The present invention will be better understood by reference to the Detailed Description Section of this Specification, with reference to the Drawings.

The present invention will be better understood by reference to the Detailed Description Section of this Specification, in combination with the Drawings.

DETAILED DESCRIPTION

Figure 1:
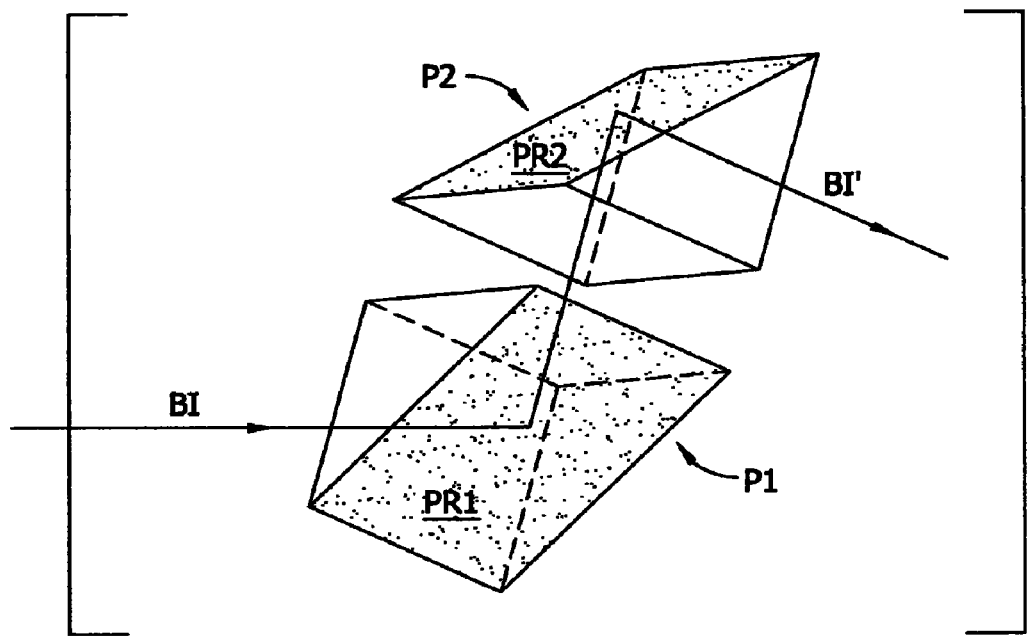
FIG. 1 shows two Prisms (P1) (P2) having reflective sides (PR1) and (PR2) respectively.
Figure 2:
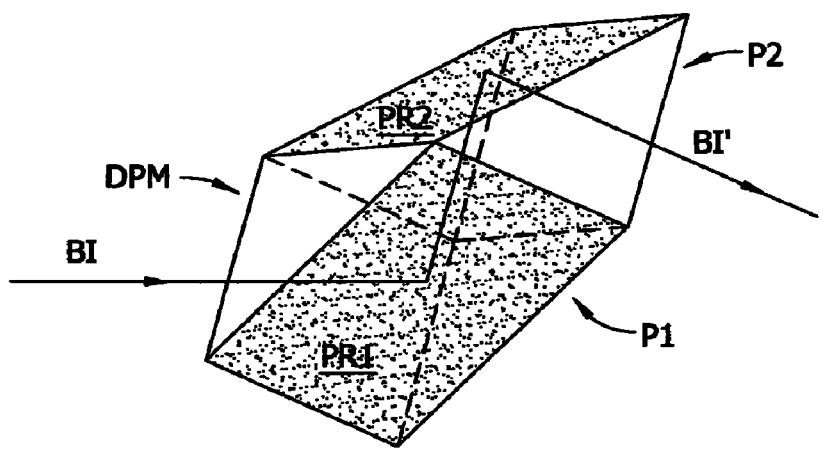
FIG. 2 shows the two Prisms of FIG. 1 merged into a Dual Prism Means (DPM) of the present invention.
Figure 3:
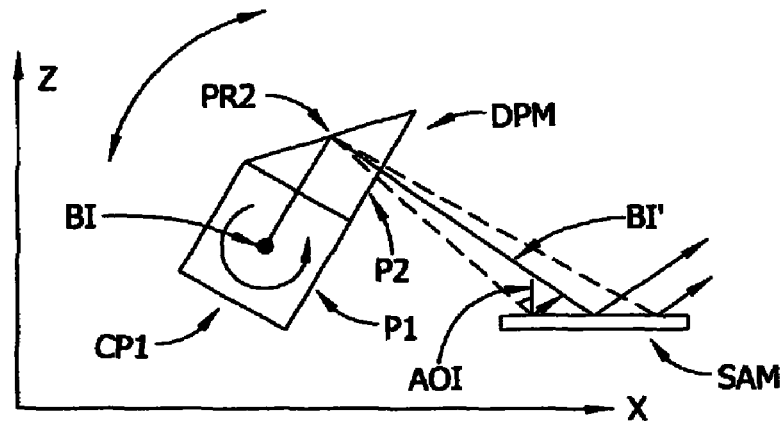
FIG. 3 demonstrates a Dual Prism Means (DPM) configured to provide a polarized output beam in a "X"-"Z" plane, by re-directing an input beam which enters thereinto along a "Y" axis, in an "X"-"Y"-"Z" coordinate system.

Turning now to the Drawings, FIG. 1 shows two Prisms (P1) (P2) having reflective sides (PR1) and (PR2) respectively. Also shown are Input (BI) and Output (BI') Beams into and out of said Prisms. While said system of two Prisms (P1) (P2) can be used directly in the present invention, FIG. 2 shows the two Prisms of FIG. 1 merged into a more convenient to use Dual Prism Means (DPM). Said Dual Prism Means (DPM) is configured to provide a polarized output beam in a "X"-"Z" plane, by re-directing an input beam which enters thereinto along a "Y" axis, in an arbitrary "X"-"Y"-"Z" coordinate system. To understand the system, reference is made to FIG. 1 wherein Beam (BI) is shown to enter a face of (P1) along a perpendicular to said face, and it then reflects from side (PRI) in (P1), and proceeds toward Prism (P2), enters a face thereof along a perpendicular thereto, then reflects from side (PR2) thereof, and exits (P2) as beam (BI'). The embodiment of FIG. 2 performs a similar function, but the face of Prism (P2) which the beam enters in FIG. 1 is no longer present. It is to be understood that a plane containing input beam (BI), (say originating in the "X"-"Y" plane), can be rotated about the locus of said input beam (BI), and a plane Parallel to that plane contains (BI'). That is, if a plane containing input beam (BI) is considered to begin in an "X"-"Y" plane, and that plane is rotated about the locus of (BI), a plane results which can be translated along the "Z" axis which will contain beam (BI') in the "X"-"Z" plane, and adjustment in rotation about the input beam (BI) controls the angle-of-incidence (AOI) the output beam (BI') makes with respect to a sample (SAM). FIG. 3 demonstrates this by showing Input Beam (BI) proceeding along a "Y" axis, (which projects perpendicular to the plane of the page), and entering (P1), as well as an Output Beam (BI') exiting (P2). It should be appreciated that the direction of the locus of Output Beam (BI') is parallel to, but offset from an "X"-"Y" plane containing the locus of Input Beam (BI), but which plane has been rotated about (BI). Again, the direction of the locus of said (BI') can be controlled by rotation of the combination of (P1) and (P2), (eg. DPM), about the locus of beam (BI). And again, note specifically that FIG. 3 shows "X" and "Z" axes directly, and the "Y" axis is to be understood as projecting perpendicularly to the plane of the Paper, with the Input Beam (BI) approaching the First (P1) Prism along the "Y" axis. (Note, the use of "X"-"Y"-"Z" axes herein is not to be considered limiting of any useful functional orientation of a present invention Dual Prism Means (DMP) during use, but are used merely to, for instance, facilitate discussion of relative relationships of reflective surfaces (PR1) and (PR2) thereof).

As it is an important aspect of the present invention it is emphasized that the Dual Prism Means (DPM) can be rotated around a "Y" axis locus of the "X"-"Y"-"Z" coordinate system in FIG. 3, to alter the angle at which the output beam (BI') exits therefrom in the "X"-"Z" plane. Said rotation is preferably along the input beam (BI) locus which, as mentioned above, approaches the first prism (P1) along a "Y" axis, (from the back of the plane of the paper as shown in FIG. 3). This enables adjusting the angle-of-incidence (AOI) of the exiting output beam (BI') with respect to a sample (SAM) positioned so that said output beam impinges thereonto, as shown in FIG. 3. It is also beneficial to note that the input beam (BI) can be considered to be in a beam plane that contains the "Y" axis, (eg. the "Y"-"X" plane). Rotation of that beam plane about the locus of the input beam (BI) provides the plane which is parallel to, but offset from the plane containing output beam (BI'), which reflects from surface (PR2) of (P2), (ie. the output beam (BI') projects to the sample (SAM) at an angle-of-incidence (AOI) thereto along a locus in the "X"-"Z" plane). (This insight makes it possible to avoid use of "X"-"Y"-"Z" coordinates in describing the effect of the dual prism means (DPM) on a beam of polarized electromagnetic radiation entered thereto).

At this point it is disclosed that the dual prism (DPM) can have the reflective surfaces (PR1) and (PR2) coated with a materials such as Aluminum. When this is done the physics of reflection change from total internal reflection to specular. In fact, the present invention can comprise two specularly reflecting reflectors oriented perpendicularly with respect to one another, as are the reflective surfaces (PR1) and (PR2) of the dual prisms (DMP) and be within the scope of the present invention. (Note, a more generic description provides that the planes of incidence of beams (BI) and (BI') reflecting from the reflective surfaces (PR1) and (PR2), respectively, of a present invention system are oriented perpendicular to one another).

Figure 4:
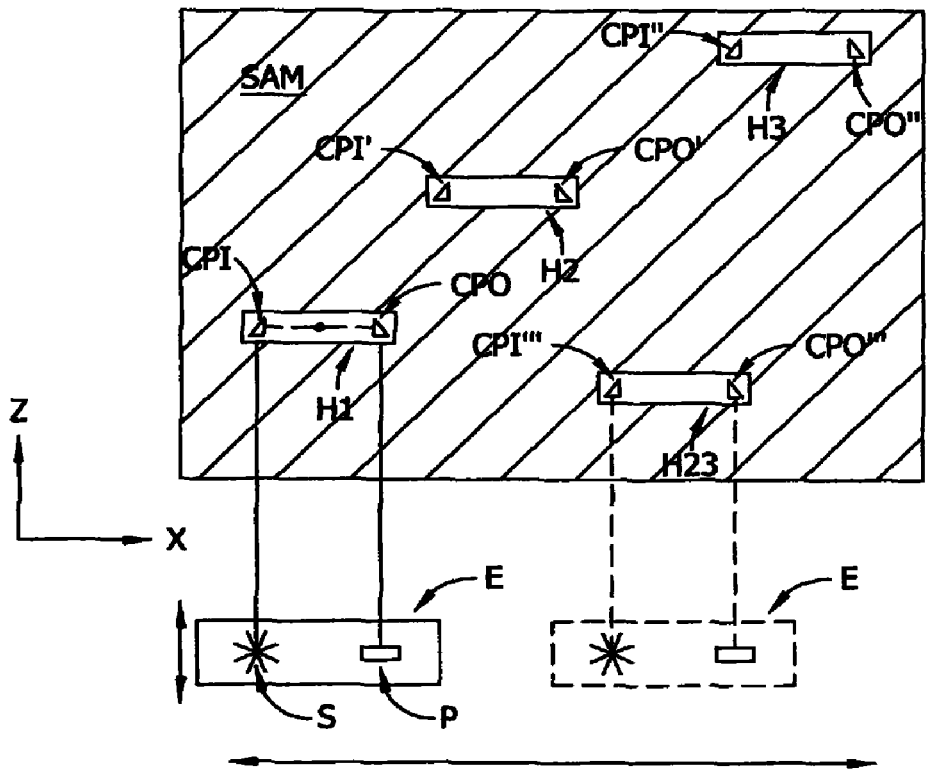
FIG. 4 shows that, in addition to a First Dual Prism means, (identified as (CPI) (CPI') (CPI") in FIG. 4), the present invention can involve a Second Dual Prism means, (identified as (CPO) (CPO') (CPO") in FIG. 4)., configured to receive a beam which reflects from a sample in a an "X"-"Z" plane, and re-direct it along a "Y" axis into a Detector (D).

Further, FIG. 4 shows that, in addition to a first dual prism means, (identified as (CPI) (CPI') (CPI") (CPI''') in FIG. 4), the present invention can involve a second dual prism means, (identified as (CPO) (CPO') (CPO") (CPO''') in FIG. 4), configured to receive a beam which reflects from a sample in an "X"-"Z" plane, and re-direct it along a "Y" axis, (ie. out of the page), into a detector (D). Four systems are shown (H1) (H2) (H3) (H23) which can be individually accessed by the ellipsometer (E), (which comprises polarization generation state source (S) and polarization state detector (D)), by moving said ellipsometer (E) in "X" and "Z" directions. Note that by adding intermediately positioned systems such as (H23), the distance the ellipsometer must be moved to access different points on the sample (SAM) is reduced. Many more such intermediately placed systems can be added.

Note that the FIG. 4 configuration enables providing an ellipsometer or polarimeter with Polarization State Generation system, (indicated generally as (S) in FIG. 4), and polarization state detection system, (indicated generally as (D) in FIG. 4), located adjacently, side by side, rather than distally positioned from one another as is the result where beam directors are not applied. And as alluded to, an additional aspect can involve positioning a plurality of first and second dual prism means near a sample, and move an ellipsometer or polarimeter adjacently located polarization state generation system (S) and polarization state detection system (D) to sequentially provide and receive, respectively, input (BI) and output (BO) electromagnetic beams.

Figure 5A:
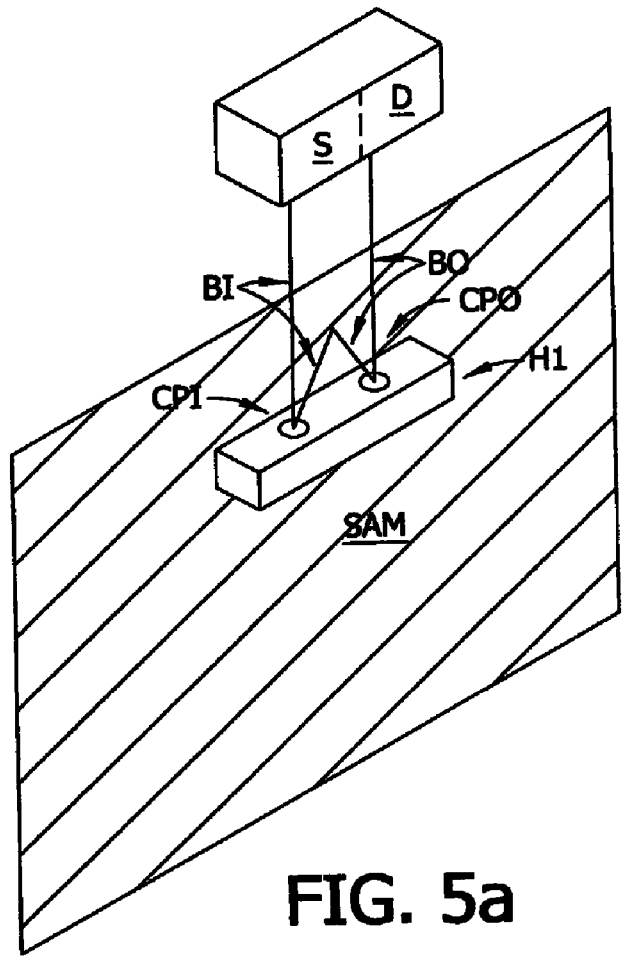
FIGS. 5a and 5b demonstrate a present invention stationary Ellipsometer (E) or polarimeter Polarization State Generation System (S) and Polarization State Detection System (D) located adjacently side by side, and a plurality of First and Second Dual Prism Means, (shown as combinations (H1) (H2) (H3)), set off from, (in a "Z" direction as shown), but shown vertically aligned with one another, and adjacent to a Sample (SAM).
Figure 5B:
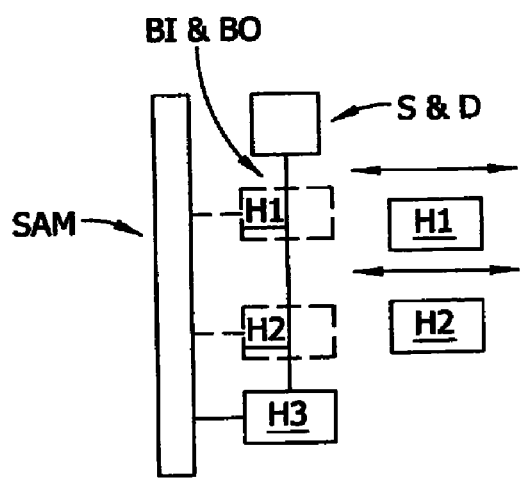

FIGS. 5a and 5b demonstrate that it is also within the scope of the present invention to provide a stationary ellipsometer or polarimeter polarization state generation system (S) and polarization state detection system (D), again located adjacently side by side, and a plurality of first and second dual prism means, (shown as combinations (H1) (H2) (H3)), set off from, (in a "Z" direction as shown), but shown vertically aligned with one another, and adjacent to a sample (SAM). In use, the first of said plurality of first and second dual prism means (H1) can be positioned to intercept the input beam (BI) such that a location on the sample (SAM) is investigated. Thereafter, the first of said plurality of first and second dual prism means can be moved to a position which allows the input beam (BI) to be intercepted by the second (H2) of the aligned plurality of first and second dual prism means so that a second location on the sample (SAM) can be investigated. Then the second (H2) of the aligned plurality of first and second dual prism means can be moved out of the path of the input beam (BI) thereby allowing a third (H3) of said plurality of first and second dual prism means to intercept the input beam (H3) so that a third location on the sample (SAM) can be investigated, and so on.

Figure 6A:
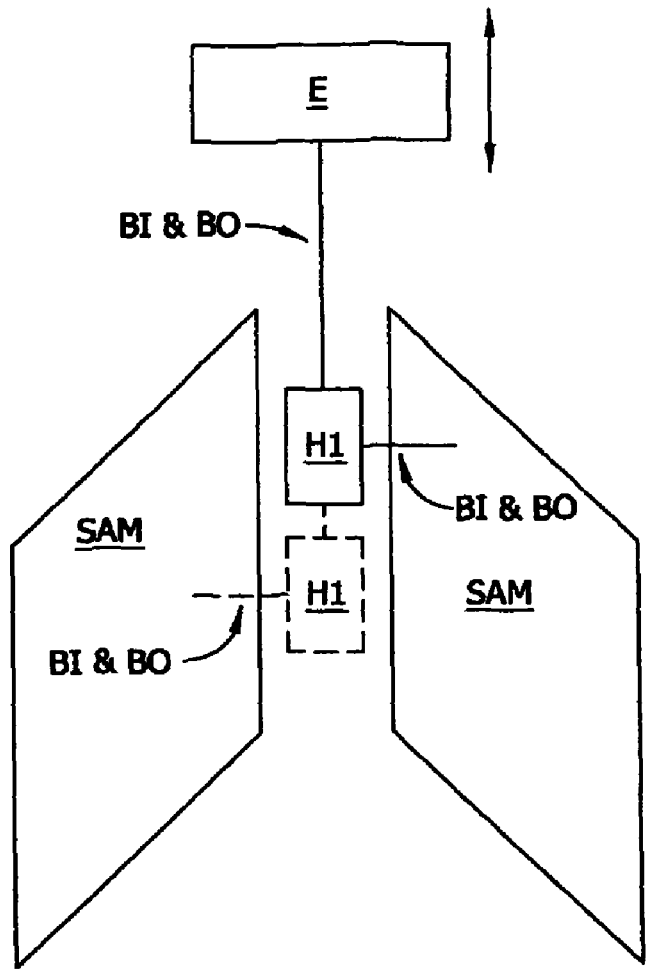
FIGS. 6a and 6b demonstrate a stationary Ellipsometer (E) or polarimeter Polarization State Generation System (S) and Polarization State Detection (D) systems located adjacently, side by side, having have a single First and Second Dual Prism Means (H1) mounted with respect thereto in a way that allows its motion in a direction parallel to the Input Beam (BI) locus so that a sequence of points along a line on a Sample (SAM) can be sequentially investigated.
Figure 6B:
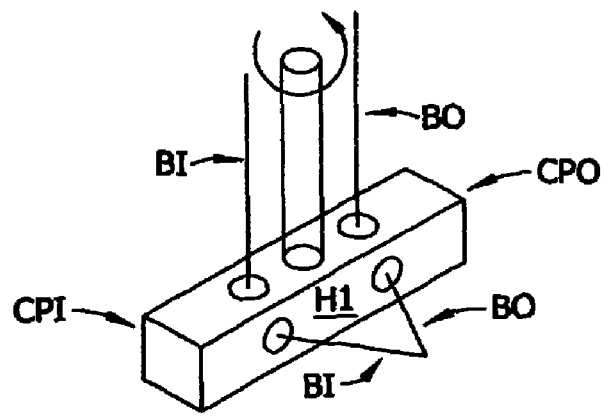

Further, FIGS. 6a and 6b demonstrate that a stationary ellipsometer or polarimeter polarization state generation system and polarization state detection systems located adjacently, side by side, can have a single first and second dual prism means (H1) mounted with respect thereto in a way that allows its motion in a direction parallel to the input beam (BI) locus so that a sequence of points along a line on a sample (SAM) can be sequentially investigated. In this embodiment said single first and second dual prism means can be mounted to allow rotation, (see FIG. 6b), along an axis parallel to the input beam (BI) locus, so that a sample (SAM) comprising such as the inside of a pipe, or perhaps two samples oriented parallel to one another can be investigated by a single first and second dual prism means (H1) which is mounted therebetween as demonstrated in FIG. 6a.

Figure 7A:
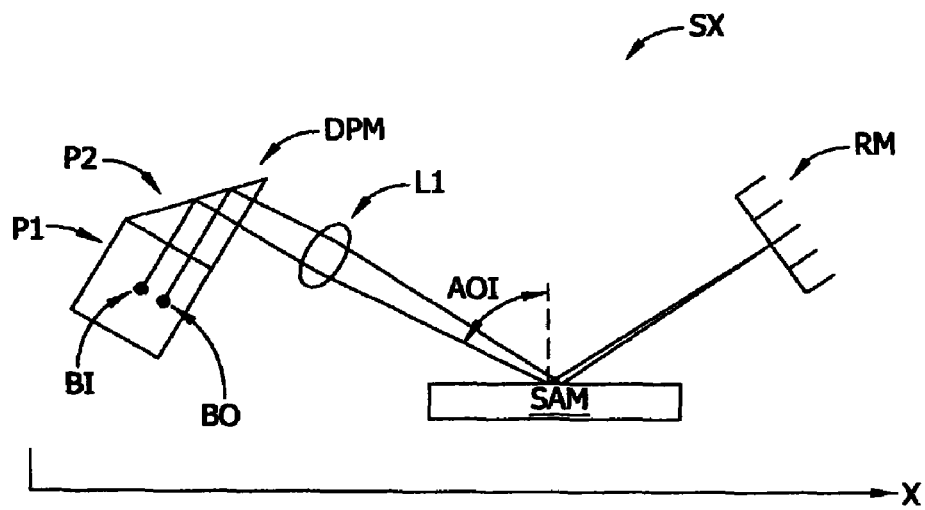
FIG. 7a shows another embodiment of the present invention System (SX) provides that a single Dual Prism Means (DPM) can be applied, in combination with a Back Reflector (RM), to direct both Input (BI) and Output (BO) Beams.

FIG. 7a shows another embodiment of the present invention provides that a single dual prism means (DPM) can be applied to direct both input (BI) and output (BO) beams. In this approach input (BI) and output (BO) beams are both directed along a "Y"-axis, (from a polarization state generator and polarization state detector, not shown), and the sample (SAM) investigating beam approaches a sample (SAM) along an angle of incidence in an "X"-"Z" plane. Between the single dual prism means (DPM) and said sample (SAM) is located a focusing means (L1), the optical axis which is off-set from a location which would direct the Input beam (BI) therealong. Further, a reflector (RM) is positioned to direct the input beam (BI), after it reflects from the sample (SAM), back toward the sample (SAM) so that it reflects from a different position thereon, then passes back through said focusing means (FL), (eg. shown as a non-limiting Lens), and back through the single dual prism means (DPM). The effect of doing this is to cause the output beam (BO) to exit the single dual prism means (DPM) offset from the input beam (BI), so it can enter a detector (D), which is offset from the source (S) of the Input Beam (BI), (see FIG. 7b).

Figure 7B:
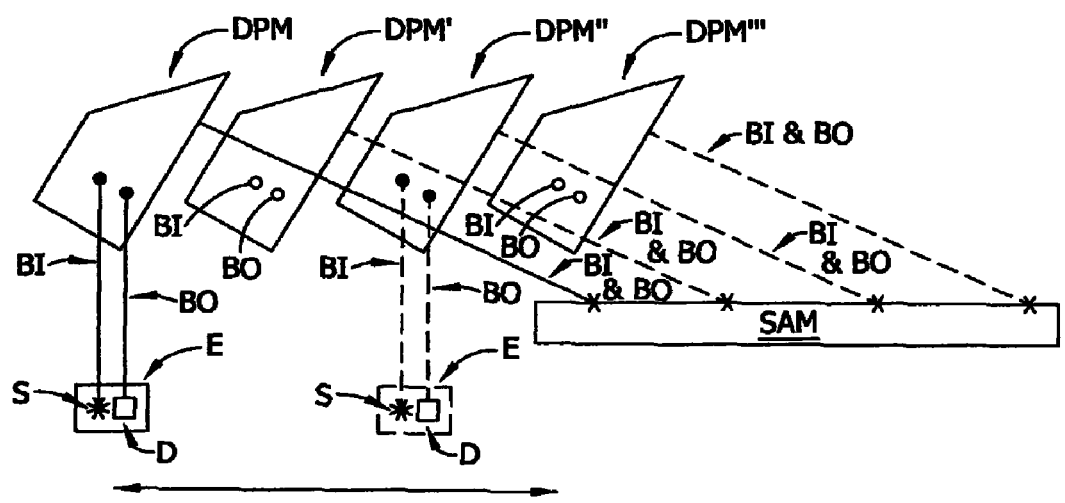
FIG. 7b shows that multiple FIG. 7a Systems (SX) can be provided and oriented with respect to one another.

FIG. 7b shows that multiple FIG. 7a type Systems can be provided, (ie. demonstrated by dual prism means (DPM) (DPM') (DPM") (DPM''') with the remaining components not shown to reduce clutter), and oriented with respect to one another so that an ellipsometer need be moved only a relatively short distance to provide and receive input (BI) and output (BO) beams from different of said dual prism means (DPM) (DPM') (DPM") (DPM''') systems, which different (DPM) (DPM') (DPM") (DPM''') systems correspond to investigation of different locations on a sample (SAM). (Note, in FIGS. 7a and 7b an ellipsometer (E) system would be mounted, for instance, at a distance perpendicular to, and in front of, the page and have the capability to move to horizontally right and left. In FIG. 7b the ellipsometer is demonstrated as below the dual prism means). It is also noted that, as in FIG. 7a, the locations of the input (BI) and output (BO) beams are very close to one another in each of the indicated (DPM) (DPM') (DPM") (DPM''') systems. An ellipsometer can utilize fiber optics to separately access said (BI's) and (BO's), or it is possible to position yet another dual prism system in one or both of the (BI) or (BO) beams from each of the multiple (DPM) (DPM') (DPM") (DPM'''), to shift the beam to an ellipsometer accessible location. Any functional approach can be used to provide signal to the ellipsometer (E).

Figure 8:
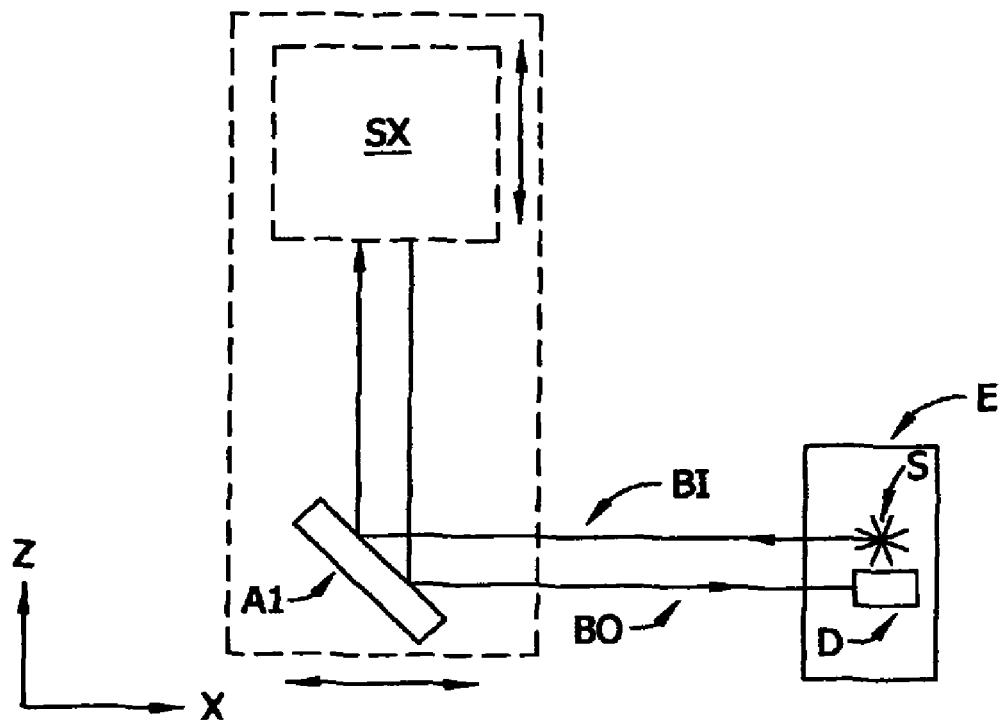
FIG. 8 shows that another embodiment within the scope of the present invention enables an approach to accessing a multiplicity of points on a Sample (SAM).

FIG. 8 shows that the present invention can apply a system comprising at least one dual prism means, (eg. (SX) of FIGS. 7a and 7b), or a system of two dual prism means such as (CPO) of FIG. 4, to enable an approach to accessing a multiplicity of points on a sample (SAM). Shown are an exemplary system comprising at least one Beam Reflection Means (A1) and a System (SX). Said reflection means (A1) and system (SX) are mounted to allow both to be moved together in an "X" direction parallel to an input beam (BI) locus, and the system (SX) can also be moved in a "Z" direction perpendicular to said input beam (BI) locus. This configuration allows investigating essentially any location on a sample (SAM) located in a plane offset from (SX), (ie. a "X"-"Z" plane positioned along a "Y" axis location projected into or out of the paper), using a stationary location ellipsometer (E).

The present invention then comprises an ellipsometer, polarimeter or the like system which comprises a combination of two (P1) (P2) Prisms, or an equivalent merged dual prism means (DPM), configured to provide a polarized output beam in a "X"-"Z" plane, by re-directing an input beam which enters thereinto along a "Y" axis, in an arbitrary "X"-"Y"-"Z" coordinate system. Importantly, it is to be appreciated that said combination of two (P1) (P2) Prisms or merged dual prism means (DPM) further provides benefit in that it substantially compensates any effects on beam polarization state entered by a first beam directing reflection therewithin, by the effects of a second beam directing reflection therewithin. This is accomplished because the effect of a first reflection on a first orthogonal component, (eg. p or s component), of a polarized beam in the dual prism means (DPM) configuration, is canceled by a similar effect in the second reflection on the other orthogonal component, (eg. an s or p component, respectively). For example, if the first reflection has an effect on a p orthogonal component, the second reflection has a compensating effect on the s orthogonal component, and vice-versa.

Figure 9:
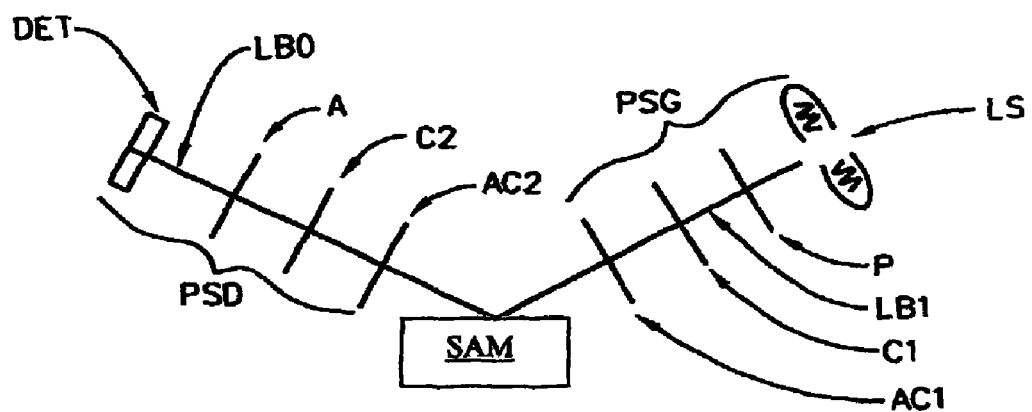
FIG. 9 is included to show the basic elements of an ellipsometer or polarimeter.

FIG. 9 is included to show the basic elements of an ellipsometer or polarimeter. Shown are a source of a beam of electromagnetic radiation (LS), a polarizer (P), a possible first compensator (C1), first possible additional components (AC1), a sample (SS), second possible additional components (AC2), a possible second compensator (C1), an analyzer (A) and a detector (DET). Note a grouping of elements (LS) (P) (C1) and (AC1) are identified as a polarization state generator (PSG) and a grouping of elements (A) (C2) (AC2) and (DET) are identified as a polarization state detector (PSG). Also indicated are input beam (LB1) before the sample (SAM) and output beam (LBO) thereafter.

Figure 10:
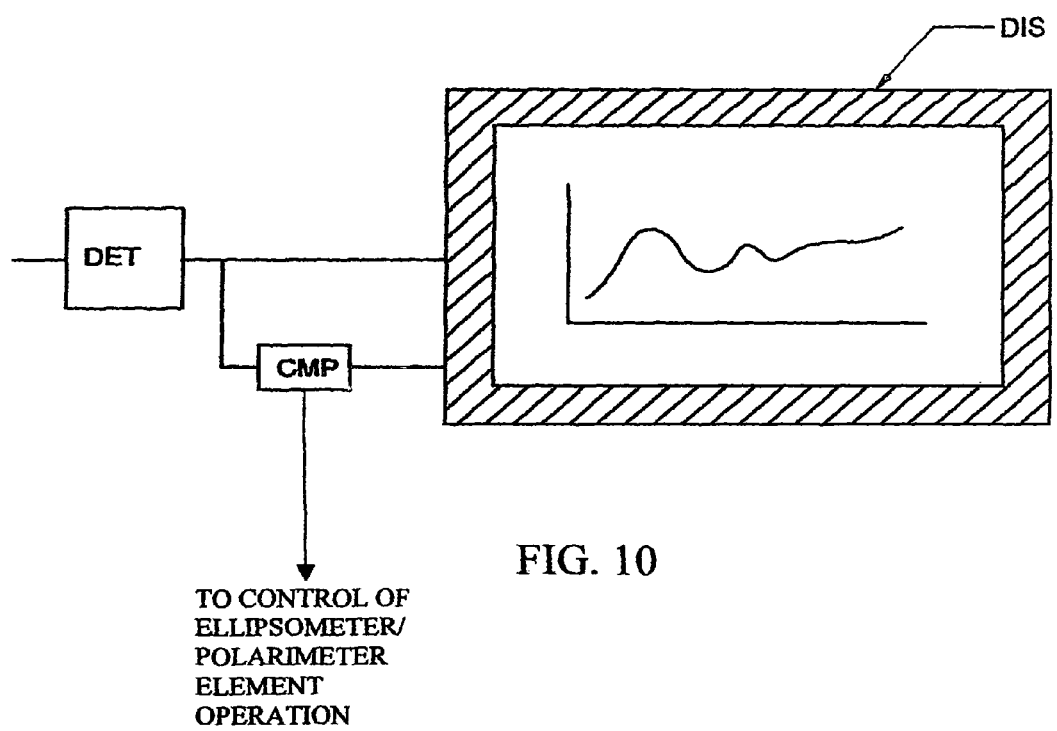
FIG. 10 is included to show that the system of the present invention can be controlled by a computer.

FIG. 10 is included to show that the system of the present invention can be controlled by a Computer (CMP) and that results of applying the present invention which result in data being produced by said Detector (DET), or analyzed results thereof, can be presented in a Display (DIS).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An ellipsometer or polarimeter system which comprises a first dual reflection surface means selected from the group consisting of:
   first and second separate reflection surfaces; and
   a single element having first and second reflection surfaces;
configured to provide a polarized output beam in an "X"-"Z" plane, by redirecting an input beam which enters thereinto along a "Y" axis, in an "X"-"Y"-"Z" axis coordinate system, said first dual reflection surface means further serving to substantially compensate any effects on beam polarization state entered by a first beam direction reflection therewithin, by effects of a second beam directing reflection therewithin, a mechanism thereof being that an effect of the first reflection on a p or s component of a polarized beam in the dual reflection surface means configuration, is canceled by a similar effect in the second reflection on an s or p component, respectively;
said first dual reflection surface means being characterized in that projected planes of the first and second reflection surfaces thereof simultaneously:
   intersect the "Y" axis and the "Z" axis but not the "X" axis at a single point thereof, and
   intersect the "X" axis and the "Z" axis but not the "Y" axis at a single point thereof,
respectively, and in that said second reflection surface is translated from the first reflection surface along the "Z" axis as said first dual reflection surface means is viewed in frontal elevation;
said first dual reflection surface means being mounted to allow rotation about a locus of the input beam to alter an angle at which the output beam exits from the second reflection surface in said "X"-"Z" plane.

2. An ellipsometer or polarimeter system as in claim 1, in which said rotation is along the input beam locus, which enables adjusting an angle-of-incidence (AOI) of an exiting beam with respect to a sample positioned so that said output beam impinges thereonto.

3. An ellipsometer or polarimeter system as in claim 1, which further comprises a second dual reflection means positioned to receive a beam which reflects in an "X"-"Z" plane from a sample, and re-direct the beam parallel to said input beam "Y" axis into a detector, thereby enabling an ellipsometer or polarimeter with polarization state generation and polarization state detection systems to be located adjacently, side by side.

4. An ellipsometer or polarimeter system, as in claim 1 in which the first dual reflection means is selected from the group consisting of:
   a first dual prism means configured to provide a polarized output beam along a locus parallel to a plane resulting from rotating a first beam plane about the locus of said input beam, said reflections being based on total internal reflection;
   a first dual prism means configured to provide a polarized output beam along a locus in a plane parallel to a plane resulting from rotating a first beam plane about the locus of said input beam, said reflections being based on specular reflection;
   a first dual reflecting means comprising two beam directing reflection surfaces, which reflection surfaces are specularly reflecting and are configured to provide a polarized output beam along a locus parallel to a plane resulting from rotating a first beam plane about the locus of said input beam;
said two beam directing reflection surfaces being oriented in planes which are perpendicular to one another.

5. An ellipsometer or polarimeter system as in claim 1 in which the "X"-"Y"-"Z" axes are arbitrary with respect to any lab coordinates, but serve only to identify orthogonal relationships within said first dual reflection surface means.

6. An ellipsometer or polarimeter system as in claim 2 in which the "X"-"Y"-"Z" axes are arbitrary with respect to any lab coordinates, but serve only to identify orthogonal relationships within said first dual reflection surface means.

7. An ellipsometer or polarimeter system as in claim 3 in which the "X"-"Y"-"Z" axes are arbitrary with respect to any lab coordinates, but serve only to identify orthogonal relationships within said first and second dual reflection means.

8. An ellipsometer or polarimeter system as in claim 4 in which the "X"-"Y"-"Z" axes are arbitrary with respect to any lab coordinates, but serve only to identify orthogonal relationships within said first dual reflection surface means.

9. An ellipsometer or polarimeter system comprising a stationary polarimeter or stationary ellipsometer having a polarization state generator and a polarization state detector located adjacently, side by side, said ellipsometer or polarimeter system further comprising a plurality of combinations of first and second dual prism means, each of the dual prism means thereof being constructed as a selection from the group consisting of:
  each of the dual prism means consists of two separate prisms; and
  each of the dual prism means consists of a single element;
the first dual prism means in each of the plurality thereof being associated with the polarization state generator such that a beam received thereby from the polarization state generator is directed to impinge on a sample, and the second dual prism means in each of the plurality thereof being associated with the polarization state detector such that a beam reflecting from said sample is directed thereby to the polarization state detector;
said first and second dual prism means in each of the plurality of combinations thereof being aligned with one another adjacent to said sample such that, in use, a first combination of first and second dual prisms means is positioned to intercept an input beam such that a first location on the sample is investigated, and thereafter, the first combination of said first and second dual prism means can be moved to a position which allows an input beam to be intercepted by a second combination of first and second dual prisms means so that a second location on the sample is investigated;
each first dual prism means of said plurality of combinations of said first and second dual prism means being characterized in that a polarized output beam in a "X"-"Z" plane is produced by re-directing an input beam which enters thereinto along a "Y" axis, in an "X"-"Y"-"Z" coordinate system; each of said dual prism means further serving to substantially compensate any effects on beam polarization state entered by a first beam directing reflection therewithin, by effects of a second beam directing reflection therewithin, a mechanism thereof being that an effect of the first reflection on a p or s component of a polarized beam in each of said dual prism means configuration, is canceled by a similar effect in the second reflection on an s or p component respectively;
each of plurality of combinations of said first and second dual prism means being mounted with respect to said stationary ellipsometer or stationary polarimeter that allows motion in a direction parallel to a locus of the input beam so that a sequence of points along a line on a sample can be sequentially investigated.

10. An ellipsometer or polarimeter system as in claim 9, wherein said second combination of first and second dual prism means also can be be moved out of a path of the input beam thereby allowing a third of combination of first and second dual prism means to intercept the input beam so that a third location on the sample can be investigated.

11. An ellipsometer or polarimeter system comprising a stationary ellipsometer or stationary polarimeter having a polarization state generator and a polarization state detector located adjacently, side by side, having a first and second dual prism means, each of the dual prism means comprising a selection from the group consisting of:
  two separate prisms; and
  a single element;
the first dual prism means configured to provide a polarized output beam in an "X"-"Z" plane, by re-directing an input beam which enters thereinto along a "Y" axis, in an "X"-"Y"-"Z" coordinate system; each of said first and second dual prism means further serving to substantially compensate any effects on beam polarization state entered by a first beam directing reflection therewithin, by effects of a second beam directing reflection therewithin, a mechanism thereof being that an effect of the first reflection on a p or s component of a polarized beam in each of the first and second dual prism means configuration, is canceled by a similar effect in the second reflection on an s or p component respectively;
said first and second dual prism means each being mounted with respect to said stationary ellipsometer or stationary polarimeter that allows motion in a direction parallel to a locus of the input beam so that a sequence of points along a line on a sample can be sequentially investigated.

12. An ellipsometer or polarimeter system as in claim 11, in which said first and second dual prism means are mounted to further allow rotation along an axis parallel to the locus of the input beam, so that a sample comprising an inside of a pipe, or two samples oriented parallel to one another can be investigated.

13. An ellipsometer or polarimeter system comprising a single dual prism means which comprises a selection from the group consisting of:
  two separate prisms; and
  a single element;
configured to provide a polarized output beam in an "X"-"Z" plane, by re-directing an input beam which enters thereinto along a "Y" axis, in an "X"-"Y"-"Z" coordinate system; said dual prism means further serving to substantially compensate any effects on beam polarization state entered by a first beam directing reflection therewithin, by effects of a second beam directing reflection therewithin, a mechanism thereof being that an effect of the first reflection on a p or s component of a polarized beam in the dual prism means configuration, is canceled by a similar effect in the second reflection on an s or p component, respectively;
which single dual prism means is applied to direct both input and output beams which are directed parallel to the "Y" axis and wherein a sample investigating beam approaches a sample along an angle of incidence in the "X"-"Z" plane, there being, between the single dual prism means and said sample a focusing means, an optical axis of which is off-set from a location which would direct the input beam thereal-ong, said ellipsometer or polarimeter system further comprising a reflector positioned to direct the input beam, after the input beam reflects from the sample, back toward the sample so that said input beam reflects from a different position thereon, then passes back through said focusing means, and back through the single dual prism means, an effect thereof being to cause the output beam to exit the single dual prism means offset from the input beam, so said output beam can enter a detector which is offset from a source of the input beam.

14. A method comprising the steps of:
a) providing an ellipsometer or polarimeter system which comprises a first dual reflection surface means selected from the group consisting of:
two separate reflection surfaces; and
a single element having two reflection surfaces;
said first dual reflection surface means being selected from the group consisting of:
a first dual prism means configured to provide a polarized output beam along a locus parallel to a plane resulting from rotating a first beam plane about a locus of an input beam, reflections being based on total internal reflection;
a first dual prism means configured to provide a polarized output beam along a locus in a plane parallel to a plane resulting from rotating a first beam plane about a locus of an input beam, reflections being based on specular reflection;
a first dual reflecting means comprising two beam directing reflection surfaces, which reflection surfaces are specularly reflecting and are configured to provide a polarized output beam along a locus parallel to a plane resulting from rotating a first beam plane about a locus of an input beam;
said two beam directing reflection surfaces being oriented in planes which are perpendicular to one another and said first dual reflection surface means being configured to provide a polarized output beam in an "X"-"Z" plane, by redirecting an input beam which enters thereinto along a "Y" axis, in an "X"-"Y"-"Z" axis coordinate system; said first dual reflection surface means further serving to substantially compensate any effects on beam polarization state entered by a first beam directing reflection therewithin, by effects of a second beam direction reflection therewithin, a mechanism thereof being that an effect of the first reflection on a p or s component of a polarized beam in the first dual reflection surface means configuration, is canceled by a similar effect in the second reflection on an s or p component, respectively;
said first dual reflection surface means being characterized in that projected planes of the first and second reflection surfaces thereof simultaneously:
intersect the "Y" axis and the "Z" axis but not the "X" axis at a single point thereof, and
intersect the "X" axis and the "Z" axis but not the "Y" axis at a single point thereof,
respectively, and in that said second reflection surface is translated from the first reflection surface along the "Z" axis as said first dual reflection surface means is viewed in frontal elevation;
said first dual reflection surface means being mounted to allow rotation to alter an angle at which the output beam exits therefrom, said rotation being along a locus of the input beam, which enables adjusting of an angle-of-incidence (AOI) of an exiting beam with respect to a sample positioned so that said output beam impinges thereonto;
b) causing a polarized beam to enter said first dual reflection surface means along the locus parallel to the "Y" axis, such that said beam reflects from twice therewithin an exits in the "X"-"Z" plane.

15. A method as in claim 14, wherein the provided ellipsometer or polarimeter system further comprises a second dual reflection means positioned to receive a beam which reflects from the sample in the "X"-"Z" plane, and re-direct the beam parallel to said input beam "Y" axis into a detector, thereby enabling an ellipsometer or polarimeter with a polarization state generation and a polarization state detection system to be located adjacently, side by side.

16. A method comprising the steps of:
a) providing a system comprising:
a1) a movable ellipsometer or a movable polarimeter system comprising:
a polarization state generator; and
a polarization state detector;
oriented adjacently side by side and separated by a fixed predetermined distance therebetween, such that in use a position of said movable ellipsometer or said movable polarimeter system polarization state generator and polarization state detector can be moved as a unit;
a2) a sample;
a3) at least two beam directing means, each beam directing means comprising first and second dual reflection surface means, selected from the group consisting of:
two separate reflection surfaces; and
a single element having two reflection surfaces;
each of said first dual reflection surface means being configured to provide a polarized output beam in an "X"-"Z" plane, by re-directing an input beam which enters thereinto along a "Y" axis, in an "X"-"Y"-"Z" coordinate system; each of the first and second dual reflection surface means further serving to substantially compensate any effects on beam polarization state entered by a first beam directing reflection therewithin, by effects of a second beam directing reflection therewithin, a mechanism thereof being that an effect of the first reflection on a p or s component of a polarized beam in each of the first and second dual reflection surface means configuration, is canceled by a similar effect in the second reflection on an s or p component, respectively;
the first and second dual reflection surface means in each beam directing means further being oriented adjacently side by side and separated by a fixed predetermined distance therebetween which is appropriate to allow a beam of electromagnetic radiation from said polarization state generator to enter one thereof, be directed thereby to reflect from a sample, enter the second thereof, and be directed thereby into the polarization state detector;
b) positioning said at least two beam directing means at locations offset from one another in two dimensions;
c) moving said movable ellipsometer or said movable polarimeter system into a position such that a beam of electromagnetic radiation from said polarization state generator enters one of said first and second dual reflection surface means of one of said at least two beam directing means, is directed thereby to reflect from said sample, enter the other of said first and second dual reflection surface means of the one of said at least two beam directing means thereof and be directed thereby into the polarization state detector;
d) moving said movable ellipsometer or polarimeter system into a position such that a beam of electromagnetic radiation from said polarization state generator enters one of said first and second dual reflection surface means of another of said at least two beam directing means, is directed thereby to reflect from said sample, enter the other of said first and second dual reflection surface means of the other of said at least two beam directing means thereof and be directed thereby into the polarization state detector;
to an end that said polarization state detector produces an output signal.

17. A method as in claim 16, wherein the step of providing a system further involves providing at least a third beam directing means, which is functionally similar to the first and second beam directing means;

and wherein said method further comprises:

e) moving said movable ellipsometer or said movable polarimeter system into a position such that a beam of electromagnetic radiation from said polarization state generator enters one of said first and second dual reflection surface means of said third beam directing means, is directed thereby to reflect from said sample, enter the other of said first and second dual reflection surface means of the third beam directing means thereof and be directed thereby into the polarization state detector;

to the end that said polarization state detector produces an output signal.

\* \* \* \* \*